United States Patent
Curulla-Ferre et al.

(10) Patent No.: US 10,668,450 B2
(45) Date of Patent: *Jun. 2, 2020

(54) SUPPORTED INDIUM OXIDE CATALYST AND PROCESS FOR METHANOL SYNTHESIS USING THE SAME

(71) Applicants: TOTAL RAFFINAGE CHIMIE, La Défense (FR); ETH ZURICH, Zurich (CH)

(72) Inventors: Daniel Curulla-Ferre, Uccle (BE); Charlotte Drouilly, Uccle (BE); Oliver Martin, Zürich (CH); Cecilia Mondelli, Zürich (CH); Javier Perez-Ramirez, Zürich (CH); Antonio J. Martin-Fernandez, Dietikon (CH)

(73) Assignee: TOTAL RAFFINAGE CHIMIE, Courbevoie (FR)

( * ) Notice: Subject to any disclaimer, the term of this patent is extended or adjusted under 35 U.S.C. 154(b) by 142 days.

This patent is subject to a terminal disclaimer.

(21) Appl. No.: 16/067,864

(22) PCT Filed: Dec. 20, 2016

(86) PCT No.: PCT/EP2016/081987
§ 371 (c)(1),
(2) Date: Jul. 3, 2018

(87) PCT Pub. No.: WO2017/118572
PCT Pub. Date: Jul. 13, 2017

(65) Prior Publication Data
US 2020/0061582 A1 Feb. 27, 2020

(30) Foreign Application Priority Data
Jan. 7, 2016 (EP) .................................... 16150481

(51) Int. Cl.
| | | |
|---|---|---|
| *C07C 29/151* | (2006.01) | |
| *C07C 29/153* | (2006.01) | |
| *B01J 23/08* | (2006.01) | |
| *B01J 21/06* | (2006.01) | |
| *B01J 37/08* | (2006.01) | |
| *B01J 37/02* | (2006.01) | |
| *B01J 37/03* | (2006.01) | |
| *B01J 35/10* | (2006.01) | |

(52) U.S. Cl.
CPC ............ *B01J 23/08* (2013.01); *B01J 21/066* (2013.01); *B01J 35/1014* (2013.01); *B01J 35/1019* (2013.01); *B01J 35/1038* (2013.01); *B01J 35/1042* (2013.01); *B01J 35/1047* (2013.01); *B01J 37/0203* (2013.01); *B01J 37/031* (2013.01); *B01J 37/088* (2013.01); *C07C 29/151* (2013.01); *C07C 29/153* (2013.01)

(58) Field of Classification Search
None
See application file for complete search history.

(56) References Cited

U.S. PATENT DOCUMENTS 5,506,273 A 4/1996 Haruta et al.
7,279,138 B2 10/2007 Pagani et al.

FOREIGN PATENT DOCUMENTS

| EP | 2257366 B1 | 7/2011 |
|---|---|---|
| GB | 706599 A | 3/1954 |
| GB | 1159035 A | 7/1969 |
| GB | 1496379 A | 12/1977 |

OTHER PUBLICATIONS

Ye, J. et al. "Active Oxygen Vacancy Site for Methanol Synthesis from CO2 Hydrogenation on In2O3(110): A DFT Study" ACS Catal. 2013, 3, 1296-1306 (Year: 2013).*
Chen, M. et al. "Study in support effect of In2O3/MOx (M=Al, Si, Zr) catalysts for dehydrogenation of propane in the presence of CO2" Applied Catalysis A: General 407 (2011) 20-28 (Year: 2011).*
International Search Report issued in PCT/EP2016/081987, dated Mar. 28, 2017, 3 pages.
Dubois, J. L. et al.; "CO2 Hydrogenation over Carbide Catalysts"; Chem. Lett. 1992, 21, pp. 5-8.
Sahibzada, M. et al., "Methanol Synthesis from CO/CO2/H2 over Cu/ZnO/Al2O3 at Differential and Finite Conversions"; J. Catal, 1998, 174, pp. 111-118.
Toyir, J. et al.; "Highly effective conversion of CO2 to methanol over supported and promoted copper-based catalysts: influence of support and promoter"; Appl. Catal., B 2001, 29, pp. 207-215.
Sloczyński, J. et al.; "Catalytic activity of the M/(3ZnOZrO2) system (M=Cu, Ag, Au) in the hydrogenation of CO2 to methanol"; Appl. Catal., A 2004, 278, pp. 11-23.
Liang, X. L. et al.; "Carbon nanotube-supported Pd—ZnO catalyst for hydrogenation of CO2 to methanol"; Appl. Catal., B 2009, 88, pp. 315-322.
Jia, L. et al.; "Carbon dioxide hydrogenation to methanol over the pre-reduced LaCr0.5Cu0.5O3 catalyst" Catal. Comm. 2009, 10, pp. 2000-2003.
Martin, O. and Pérez-Ramérez, J.; "New and revisited insights into the promotion of methanol synthesis catalysts by CO2"; Catal. Sci. Technol. 2013, 3, pp. 3343-3352.
Ye, J. et al.; "Active Oxygen Vacancy Site for Methanol Synthesis from CO2 Hydrogenation on In2O3 (110): a DFT study"; ACS Catal. 2013, 3, pp. 1296-1306.
Martin, O. et al.; "Zinc-rich copper catalysts promoted by gold for methanol synthesis"; ACS Catal. 2015, 5, pp. 5607-5616.
Sun, K. et al., "Hydrogenation of CO2 to methanol over In2O3 catalyst" J. CO2 Util. 2015, 12, pp. 1-6.

* cited by examiner

*Primary Examiner* — Medhanit W Bahta
(74) *Attorney, Agent, or Firm* — Albert Shung

(57) ABSTRACT

The invention relates to a process for methanol synthesis comprising the steps of providing a syngas feed stream comprising hydrogen and carbon oxides selected from carbon dioxide or a mixture of carbon dioxide and carbon monoxide, wherein carbon dioxide represents from 1 to 50 mol % of the total molar content of the feed stream, carbon monoxide is contained from 0 to 85 mol % of the total molar content, and $H_2$ is comprised from 5 to 95 mol % of the total molar content of the feed stream, and a catalyst comprising indium oxide ($In_2O_3$) on a support wherein the support comprises zirconium dioxide or is zirconium dioxide; putting in contact said stream with said supported catalyst at a reaction temperature of at least 373 K (99.85° C.) and under a pressure ranging of at least 1 MPa; and recovering the methanol effluents. The invention also relates to a supported indium oxide catalyst.

11 Claims, 6 Drawing Sheets

SUPPORTED INDIUM OXIDE CATALYST AND PROCESS FOR METHANOL SYNTHESIS USING THE SAME

CROSS-REFERENCE TO RELATED APPLICATIONS

This application is a National Stage Entry of PCT/EP2016/081987, filed on Dec. 20, 2016; which itself claims priority from EP 16150481.6, filed on Jan. 7, 2016. The entireties of both PCT/EP2016/081987 and EP 16150481.6 are incorporated herein by reference.

FIELD OF THE INVENTION

The present invention relates to a process for synthesis of methanol from $CO_2$-containing syngas. It also relates to the supported catalyst used in such process.

BACKGROUND OF THE INVENTION

Methanol is widely used in different applications such as: the synthesis of formaldehyde, which is then involved in the manufacture of plastic materials, paints, and textiles, for instance; the production of dimethylether, which may be used in aerosols or as an alternative fuel for diesel engines; the transesterification of triglycerides to produce biodiesel; or as a solvent or a fuel for engines.

Methanol is commercially produced from synthesis gas (syngas), i.e., a mixture of carbon oxide (i.e., carbon monoxide (CO) and/or carbon dioxide ($CO_2$)) and hydrogen ($H_2$) that can be produced from a variety of carbonated sources. CO and $CO_2$ react with $H_2$ according to the following equations:

$$CO + 2H_2 = CH_3OH \quad (1)$$

$$CO_2 + 3H_2 = CH_3OH + H_2O \quad (2)$$

$$CO + H_2O = CO_2 + H_2 \quad (3)$$

wherein the third one corresponds to the water-gas shift (WGS) reaction.

A widely used catalyst is $Cu/ZnO/Al_2O_3$ (herein after "CuZnAl"), described for instance in GB1159035.

Usually, a syngas feed stream containing about 3 vol % $CO_2$ is used in the methanol synthesis process. This amount of 3 vol % is an optimal value since it is has been demonstrated that increasing the content of $CO_2$ in the syngas feed is detrimental to methanol productivity with CuZnAl catalyst due to the large amount of co-produced water, which strongly inhibits the catalyst activity and results in the loss of catalyst stability (Sahibzada, M. et al.; *J. Catal.* 1998, 174, 111-118; Martin, O. and Perez-Ramirez, J.; *Catal. Sci. Technol.* 2013, 3, 3343-3352). Water is produced directly in the hydrogenation of $CO_2$ to methanol, and also in the reverse water-gas shift (RWGS) reaction which competes with the hydrogenation reaction.

It would be desirable to use larger amounts of $CO_2$ in the production of methanol because $CO_2$ is a green-house gas intimately related to industrial activity and modern society and therefore such a use could help in reducing the $CO_2$ footprint of industries.

Most of the current research in methanol synthesis from $CO_2$ has been focusing on the optimization of the commercially-available CuZnAl catalyst to prevent its deactivation in the presence of water or to inhibit the RWGS reaction, as described for example in "*Zinc-rich copper catalysts promoted by gold for methanol synthesis*" by Martin, O. et al.; *ACS Catal.* 2015, 5, 5607-5616.

In spite of the improvements, these issues have not been overcome entirely. Thus, novel catalyst formulations have been investigated, such as: $Cu—ZnO—Ga_2O_3/SiO_2$ in Toyir, J. et al.; *Appl. Catal., B* 2001, 29, 207-215; or Pd—ZnO/CNT in Liang, X. L. et al.; *Appl. Catal., B* 2009, 88, 315-322; or Cu/TaC in Dubois, J. L. et al.; *Chem. Lett.* 1992, 21, 5-8; or $LaCr_{0.5}Cu_{0.5}O_3$ in Jia, L. et al.; *Catal. Comm.* 2009, 10, 2000-2003.

Of these, only $Cu—ZnO—Ga_2O_3/SiO_2$ displayed both high activity and selectivity (99.5%). However, also optimized catalysts with low Cu content have been shown to suffer from $H_2O$ inhibition, limiting their exploitation only at low conversion levels (Martin et al.; *ACS Catal.* 2015, 5, 5607-5616). Moreover, little or no data exist to evaluate the long-term stability of such catalysts in the $CO_2$ hydrogenation reaction to methanol.

Indium oxide ($In_2O_3$) has recently been identified as a potential good catalyst for $CO_2$ hydrogenation into methanol based on density-functional-theory calculations in "*Active Oxygen Vacancy Site for Methanol Synthesis from $CO_2$ Hydrogenation on $In_2O_3$(110): a DFT study*" Ye, J. et al.; *ACS Catal.* 2013, 3, 1296-1306. This study indicates that the oxygen-defective $In_2O_3$(110) surface can activate $CO_2$ and hydrogenate it via HCOO and $H_3CO$ species to methanol. An experimental study over commercially available $In_2O_3$ demonstrated reasonable $CO_2$ conversion for this catalyst but only low selectivity in "*Hydrogenation of $CO_2$ to methanol over $In_2O_3$ catalyst*" Sun, K. et al., *J. $CO_2$ Util.* 2015, 12, 1-6.

GB1496379 discloses the dehydrocyclodimerisation of C4 feedstock using a catalyst containing germanium, indium or tin metal or a compound thereof deposited on a support; it exemplifies passing isobutene over $GeO_2$, $In_2O_3$ and $SnO_2$ deposited on eta alumina.

GB706599 discloses the reaction of CO with $H_2$ using as catalysts oxides of group IVa (Ti, Zr, Hf) to which may be added activating oxides of trivalent metals; a combination of zirconium oxide with indium oxide and potassium oxide is disclosed as especially suitable. The catalyst is preferably prepared by precipitation with alkalies from an aqueous solution.

Only carbon monoxide is reacted with hydrogen. The objective stated in GB706599 is to increase the yield of isobutyl alcohol.

U.S. Pat. No. 5,506,273 relates to the hydrogenation of CO and $CO_2$ with a catalyst essentially consisting of gold and at least one metal oxide, the gold being in the form of particles deposited on the oxide, both possibly being supported; the exemplified metal oxides are ZnO, $Fe_2O_3$, $TiO_2$, $ZrO_2$, $La_2O_3$, $ZnFe_2O_4$ and $CeO_2$.

There is still a need for a process of methanol synthesis and a catalyst showing high stability, high selectivity, high activity, and low inhibition by water.

SUMMARY OF THE INVENTION

Thus it is an object of the invention to provide a new process and a new catalyst for methanol synthesis from syngas. Another object of the invention is to provide a new process allowing improvements in $CO_2$ conversion into methanol. Another object of the invention is to provide a catalyst and a process for methanol synthesis showing improvements in $CO_2$ conversion to methanol, together with high space-time yield and high selectivity to methanol. Another object of the invention is to provide a catalyst and a process for methanol synthesis showing high stability of the catalyst. The present invention provides the solution to one or more of the aforementioned needs.

According to a first aspect, the invention provides a process for methanol synthesis comprising the following steps:
providing a syngas feed stream comprising hydrogen and carbon oxides selected from carbon dioxide or a mixture of carbon dioxide and carbon monoxide, wherein carbon dioxide represents from 1 to 50 mol % of the total molar content of the feed stream, carbon monoxide is contained from 0 to 85 mol % of the total molar content, and $H_2$ is comprised from 5 to 95 mol % of the total molar content of the feed stream;
providing a catalyst comprising indium oxide ($In_2O_3$) deposited on a support wherein the support comprises zirconium dioxide or is zirconium dioxide;
putting in contact said stream with said supported catalyst at a reaction temperature of at least 373 K (99.85° C.) and under a pressure of at least 1 MPa; and
recovering the methanol effluents.

It has been found that a catalyst comprising indium oxide deposited on a support comprising zirconium dioxide may act as an efficient catalyst for $CO_2$ hydrogenation into methanol, that has none of the problems of current state-of-the-art and commercially-available methanol (CuZnAl) catalysts. Surprisingly, a synergetic effect has been demonstrated between the catalyst active phase (i.e. indium oxide) and the selected support, such that supported catalysts lead to an improved space-time yield compared to the unsupported indium oxide catalyst.

The inventive process can be performed in a CO-free syngas feed stream (i.e., containing only $CO_2$ and $H_2$), however, it has surprisingly been found that presence of CO in the syngas feed stream enhanced the $CO_2$ conversion compared to the $CO_2$ conversion in a CO-free syngas. Thus a synergetic effect between the supported catalyst and the presence of CO has been found for $CO_2$ conversion. It has also been found that presence of CO in the syngas feed stream enhanced the space time yield compared to the $CO_2$ conversion in a CO-free syngas (i.e., a syngas feed stream containing $CO_2$ and $H_2$). The process of the invention allows methanol synthesis from CO-rich syngas feed streams (i.e., wherein the $CO_2$ content is at most 30 mol % based on the total carbon oxide of the syngas feed stream) and $CO_2$-rich syngas feed streams (i.e., wherein the $CO_2$ content is above 30 mol % based on the total carbon oxide of the syngas feed stream). Therefore, the process of the present invention can be used to reduce the industrial carbon footprint.

The inventive supported catalyst has also be found to be very stable compared to prior art catalysts, so that the process can be carried out more than 1,000 hours without a significant loss in the catalyst activity, i.e., the loss in the catalyst activity is kept below 25%, preferably below 10%. It is to be noted that this stability can be achieved in both CO-rich syngas feed stream and $CO_2$-rich syngas feed stream.

With preference, one or more of the following features can be used to better define the inventive process:
The process is carried out in gaseous phase.
The reaction temperature is at least 463 K (189.85° C.), preferably at least 563 K (289.85° C.), more preferably at least 663 K (389.85° C.).
The reaction temperature is at most 773 K (499.85° C.).
The pressure is at least 2 MPa, preferably at least 3 MPa, more preferably at least 4 MPa, even more preferably at least 5 MPa.
The pressure is at most 100 MPa, preferably at most 50 MPa, more preferably at most 10 MPa.
The syngas feed stream comprises at least 3 mol % of $CO_2$ based on the total molar content of the syngas feed stream, preferably at least 5 mol %, more preferably at least 10 mol %, even more preferably at least 20 mol %.
The syngas feed comprises at most 40 mol % of $CO_2$ based on the total molar content of the syngas feed stream, preferably at most 35 mol %, more preferably at most 30 mol %.
The syngas feed stream comprises at least 1 mol % of CO based on the total molar content of the syngas feed stream, preferably at least 2 mol %, more preferably at least 10 mol %.
The syngas feed stream comprises at most 75 mol % of CO based on the total molar content of the syngas feed stream, preferably at most 65 mol %, more preferably at most 50 mol %.
The syngas feed stream comprises at least 10 mol % of $H_2$ based on the total molar content of the syngas feed stream, preferably at least 20 mol %, more preferably at least 30 mol %.
The syngas feed stream comprises at most 90 mol % of $H_2$ based on the total molar content of the syngas feed stream, preferably at most 80 mol %, more preferably at most 70 mol %, even more preferably at most 60 mol %.
The syngas feed stream comprises a mixture of carbon dioxide and carbon monoxide and the syngas feed stream contains at most 30 mol % of $CO_2$ based on the total molar content of the carbon oxide, or the syngas feed stream comprises a mixture of carbon dioxide and carbon monoxide and the syngas feed stream contains more than 30 mol % of $CO_2$ based on the total molar content of the carbon oxide.
The syngas feed stream comprises a mixture of carbon dioxide and carbon monoxide and the molar ratio of carbon monoxide to carbon dioxide (CO:CO2) in the syngas feed stream is at least 1:10, preferably at least 1:1, more preferably at least 2:1, even more preferably at least 3:1, and most preferably at least 4:1
The molar ratio of hydrogen to carbon dioxide ($H_2$:$CO_2$) in the syngas feed stream is at least 1:1, preferably it is at least 3:1, more preferably it is at least 4:1 and even more preferably at least 8:1.
The process is carried out during more than 100 hours, preferably more than 1,000 hours, more preferably more than 10,000 hours, even more preferably more than 100,000 without replacement or reactivation of the supported catalyst.
The supported catalyst exhibits a molar surface oxygen-to-indium ratio below 1.5 as determined from the atomic concentrations derived by X-ray photoelectron spectroscopy (XPS), preferably below 1.0, and more preferably below 0.8.
The catalyst consists in indium oxide deposited on a support.
The supported catalyst is a calcined supported catalyst and the support comprises zirconium dioxide ($ZrO_2$) in an amount of at least 10 wt %, preferably at least 50 wt %, more preferably at least 80 wt %, and even more preferably at least 90 wt % based on the total weight of the calcined supported catalyst.
The supported catalyst is a calcined supported catalyst and the indium oxide content in the form of $In_2O_3$ of the supported catalyst, based on total weight of the calcined supported catalyst, is ranging from 5 to 20% by weight, preferably from 5 to 15 wt %.

The supported catalyst is provided in technical shapes such as extrudates, granules, spheres, monoliths, or pellets and might contain additives such as lubricants, peptizers, plasticizers, porogens, binders, and/or fillers.

The supported catalyst is prepared by a process involving a calcination step at a temperature above 500 K (226.85° C.), preferably above 530 K (256.85° C.), more preferably above 550 K (276.85° C.), more preferably above 570 K (296.85° C.).

Prior to reaction the supported catalyst is activated in situ by raising the temperature to the reaction temperature in a flow of a gas feed stream for activation selected from inert gases, hydrogen, carbon monoxide, carbon dioxide or mixture thereof, preferably the gas feed stream for activation is or comprises an inert gas, more preferably the gas feed stream for activation is or comprises argon.

According to a second aspect, the invention relates to the use of a catalyst comprising indium oxide deposited on a support in a process for the synthesis of methanol from syngas as defined above, wherein the support comprises zirconium dioxide or is zirconium dioxide.

According to a third aspect, the invention relates to a catalyst comprising indium oxide on a support for use in a process for the synthesis of methanol from syngas wherein the catalyst support comprises zirconium dioxide or is zirconium dioxide With preference, one or more of the following features can be used to better define the inventive supported catalyst:

The supported catalyst is a calcined supported catalyst and the support comprises zirconium dioxide ($ZrO_2$) in an amount of at least 10 wt %, preferably at least 50 wt %, more preferably at least 80 wt %, and even more preferably at least 90 wt % based on the total weight of the calcined supported catalyst.

The supported catalyst comprises indium oxide containing an oxygen-defective structure and in that the molar surface ratio of oxygen to indium is below 1.5 based on the elemental atomic percent fractions as determined by X-ray photoelectron spectroscopy, preferably below 1.0 and, more preferably below 0.8.

The supported catalyst is prepared in a process involving a calcination step at a temperature above 500 K (226.85° C.), preferably above 530 K (256.85° C.), more preferably above 550 K (276.85° C.), more preferably above 570 K (296.85° C.).

The supported catalyst is a calcined supported catalyst and the indium oxide content in the form of $In_2O_3$ based on the calcined supported catalyst is ranging from 5 to 20% by weight, preferably from 5 to 15 wt %.

The supported catalyst is a calcined supported catalyst and the calcined supported catalyst has preferably a surface area (i.e. BET surface area) in the range of about 20 $m^2$ $g^{-1}$ to about 400 $m^2$ $g^{-1}$, such as from 30 $m^2$ $g^{-1}$ to about 200 $m^2$ $g^{-1}$ as determined according to $N_2$ sorption analysis according to ASTM D3663-03.

The catalyst consists in indium oxide on a support.

DETAILED DESCRIPTION OF THE INVENTION

Figure 1:
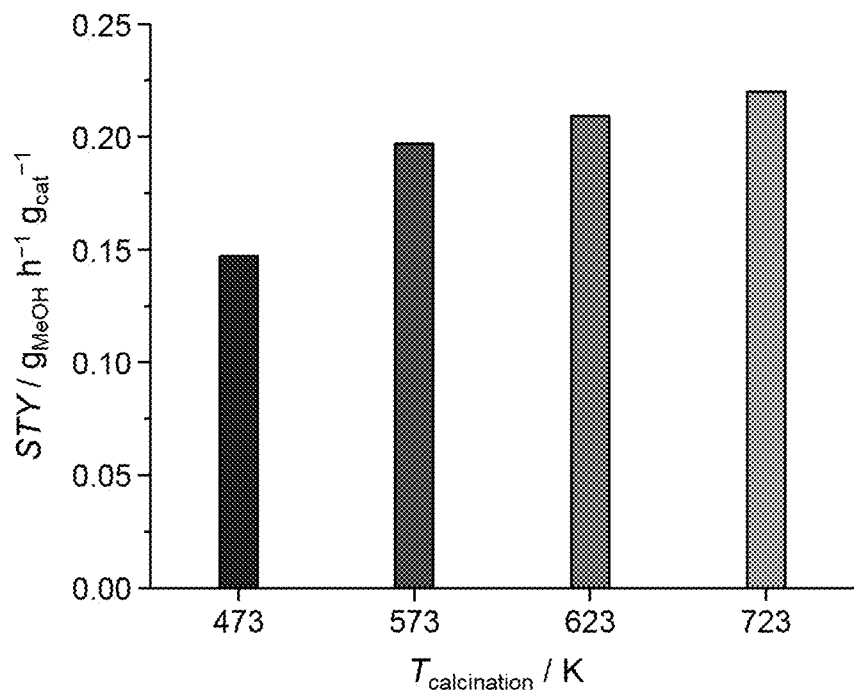
FIG. 1 is a graph reporting the space-time yield of the bulk catalysts $In_2O_3$ according to the invention as a function of the calcination temperature under standard reaction conditions (i.e., T=573 K, P=5 MPa, GHSV=21,000 $h^{-1}$, molar $H_2$:$CO_2$=4:1).

As used herein the generic term "catalyst" refers to both a "bulk" and a "supported catalyst". A bulk catalyst is a catalyst containing indium oxide without support. A supported catalyst consists of the catalyst (i.e., the catalyst comprising indium oxide) and a support. Indium oxide is the main active phase, i.e. the active phase, of the supported catalyst.

In methanol synthesis according to the invention, a feed gas composed of hydrogen gas and carbon oxides ($CO_2$ alone or a mixture of $CO_2$ and CO gases) are caused to interact on an indium oxide-based catalyst.

The invention relates to a process for methanol synthesis comprising the following steps:
- providing a syngas feed stream comprising hydrogen and carbon oxides selected from carbon dioxide ($CO_2$) or a mixture of carbon dioxide and carbon monoxide (CO), wherein carbon dioxide represents from 1 to 50 mol % of the total molar content of the feed stream, carbon monoxide is contained from 0 to 85 mol % of the total molar content, and $H_2$ is comprised from 5 to 95 mol % of the total molar content of the feed stream;
- providing a catalyst comprising indium oxide ($In_2O_3$) deposited on a support;
- putting in contact said stream with said supported catalyst at a reaction temperature of at least 373 K (99.85° C.)) and under a pressure of at least 1 MPa; and recovering the methanol effluents.

The process can be carried out in gaseous phase or in liquid phase. The solvent that can be used for the reaction in liquid phase includes hydrocarbons and other solvents which are preferably insoluble or only sparingly soluble in water. Preferably, the process is carried out in gaseous phase.

The process is carried out in a reactor comprising
- lines to introduce a syngas as feed stream to the reactor and remove products from the reactor;
- a device for heating the reactor,
- a temperature sensor and controller for detecting and controlling the temperature of the reactor at a reaction temperature of at least 373 K (99.85° C.) to 773 K (499.85° C.)
- flow controllers to control the rate of the feed stream to the reactor; and
- a pressure controller to control the reactor pressure to a pressure of at least 1 MPa.

In accordance to the invention the syngas feed stream comprises hydrogen and carbon oxides selected from carbon dioxide ($CO_2$) or a mixture of carbon dioxide and carbon monoxide. However, in a preferred embodiment, the syngas feed stream comprises hydrogen and mixture of carbon dioxide and carbon monoxide.

When the syngas feed stream comprises hydrogen and mixture of carbon dioxide and carbon monoxide, the feed stream can be CO-rich or $CO_2$-rich. In accordance to the invention, a CO-rich feed stream contains at most 30 mol % of $CO_2$ based on the total molar content of the carbon oxide whereas a $CO_2$-rich feed stream contains more than 30 mol % of $CO_2$ based on the total molar content of the carbon oxide. In a preferred embodiment of the invention, the syngas feed stream is CO-rich, i.e., the syngas feed stream contains at most 30 mol % of $CO_2$ based on the total molar content of the carbon oxide.

In a preferred embodiment the syngas feed stream contains hydrogen and carbon oxides selected from carbon dioxide or a mixture of carbon dioxide and carbon monoxide and the syngas feed stream comprises at least 3 mol % of $CO_2$ based on the total molar content of the syngas feed stream, preferably at least 5 mol %, more preferably at least 10 mol %, even more preferably at least 20 mol %.

In a preferred embodiment the syngas feed stream contains hydrogen and carbon oxides selected from carbon dioxide or a mixture of carbon dioxide and carbon monoxide and the syngas feed stream comprises at most 40 mol % of $CO_2$ based on the total molar content of the syngas feed stream, preferably at most 35 mol %, more preferably at most 30 mol %.

In a preferred embodiment the syngas feed stream contains hydrogen and carbon oxides and the syngas feed stream comprises at least 1 mol % of CO based on the total molar content of the syngas feed stream, preferably at least 2 mol %, more preferably at least 10 mol %.

In a preferred embodiment the syngas feed stream contains hydrogen and carbon oxides and the syngas feed stream comprises at most 75 mol % of CO based on the total molar content of the syngas feed stream, preferably at most 65 mol %, more preferably at most 50 mol %.

In a preferred embodiment the syngas feed stream contains hydrogen and carbon oxides selected from carbon dioxide or a mixture of carbon dioxide and carbon monoxide and the syngas feed stream comprises at least 10 mol % of $H_2$ based on the total molar content of the syngas feed stream, preferably at least 20 mol %, more preferably at least 30 mol %.

In a preferred embodiment the syngas feed stream contains hydrogen and carbon oxides selected from carbon dioxide or a mixture of carbon dioxide and carbon monoxide and the syngas feed stream comprises at most 90 mol % of $H_2$ based on the total molar content of the syngas feed stream, preferably at most 80 mol %, more preferably at most 70 mol %, even more preferably at most 60 mol %.

In a preferred embodiment, the syngas feed stream contains a mixture of carbon dioxide and carbon monoxide and the molar ratio of carbon monoxide to carbon dioxide ($CO:CO_2$) in the syngas feed stream is at least 1:10, preferably 1:1, more preferably at least 2:1, even more preferably at least 3:1, and most preferably at least 4:1.

In a preferred embodiment, the syngas feed stream contains a mixture of carbon dioxide and carbon monoxide and the molar ratio of carbon monoxide to carbon dioxide ($CO:CO_2$) in the syngas feed stream is at most 10:1, preferably at most 9:1, preferably at most 8:1.

In a preferred embodiment, the molar ratio of hydrogen to carbon dioxide in the syngas feed stream is at least 1:1, preferably it is at least 3:1, more preferably it is at least 4:1 and even more preferably at least 8:1.

The feed stream comprises $CO_2$ and Hz, or $H_2$ and a mixture of $CO_2$ and CO, preferably the feed stream may also comprise a further gaseous component such as an inert gas. The inert gas is for example argon.

In a preferred embodiment, the process is carried out at a reaction temperature of at least 463 K (189.85° C.), preferably of at least 563 K (289.85° C.), more preferably of at least 663 K (389.85° C.). The person skilled in the art may increase the reaction temperature in order to increase the conversion rate of the carbon oxides. The reaction temperature may be kept below 773 K (499.85° C.) as a good compromise between economic reasons and conversion rate achieved. However, higher reaction temperature can be contemplated. Since the methanol effluents have boiling point lower than these temperatures, methanol is recovered in the gas form, mixed with other gaseous reaction products. Preferably the methanol effluents are conducted to a condenser where they are condensed and collected. Later the methanol can be separated and purified from other reaction products by distillation.

In another preferred embodiment, the pressure is at least 2 MPa, more preferably at least 3 MPa, preferably at least 4 MPa and more preferably at least 5 MPa. The person skilled in the art may increase the pressure in order to increase the conversion rate of the carbon oxides. A good compromise between industrial feasibility and conversion rate achieved is to conduct the reaction under a pressure ranging from 5 to 10 MPa. However, higher pressure can be contemplated, such as pressure above 50 MPa or above 90 MPa. In an embodiment of the invention the pressure is at most 100 MPa. In a preferred embodiment the gas hourly space velocity (GHSV) is in the range of 1,000 to 100,000 liters at standard temperature and pressure (STP) of reactant gases per liter of supported catalyst charged to the reactor per hour, preferably 2,000 to 50,000 h$^{-1}$, more preferably 5,000 to 40,000 h$^{-1}$, and more preferably 15,000 to 40,000 h$^{-1}$.

In a preferred embodiment the process can be carried out with a stable performance with respect to activity and selectivity during more than 100 hours, preferably more than 1,000 hours, more preferably more than 10,000 hours, and even more preferably more than 100,000 hours without the need of reactivation or replacement of the supported catalyst.

In an embodiment, the process is carried out in a fixed bed or in a fluidized bed reactor comprising at least one catalytic bed. Such reactors are well-known from the person skilled in the art and for instance described in EP2257366 or in U.S. Pat. No. 7,279,138.

Catalyst and Preparation of the Catalyst

The present invention contemplates the use of supported catalyst in methanol synthesis processes wherein the syngas feed stream comprise CO or not. A supported catalyst is preferably a calcined supported catalyst thus any reference to a supported catalyst include a reference to a calcined supported catalyst. According to the invention, a supported catalyst comprises a catalyst and a support to provide mechanical support to the catalyst as well as to further enhance exposure of a feed stream to active sites of the catalyst. In such a supported configuration, an amount of the catalyst (represented as weight loading of the catalyst based on the total weight of the calcined supported catalyst) can be in the range of about 0.1 wt % to about 95 wt %.

In an embodiment, the indium oxide content in the form of $In_2O_3$ of the supported catalyst, is at least 1 wt %, preferably at least 5 wt %, more preferably at least 8 wt % based to the total weight of the calcined supported catalyst.

In an embodiment, the indium oxide content in the form of $In_2O_3$ of the supported catalyst, is at most 70 wt %, preferably at most 60 wt %, preferably of at most 50 wt %, more preferably of at most 40 wt %, even more preferably of at most 30 wt %, most preferably of at most 20 wt %, and even most preferably of at most 14 wt % based to the total weight of the calcined supported catalyst.

In an embodiment, the support comprises at least one selected from silica ($SiO_2$), alumina ($Al_2O_3$), gallium oxide ($Ga_2O_3$), cerium oxide ($CeO_2$), vanadium oxide ($V_2O_5$), chromium oxide ($Cr_2O_3$), zirconium dioxide ($ZrO_2$), titanium dioxide ($TiO_2$), magnesium oxide (MgO), zinc oxide (ZnO), tin oxide ($SnO_2$), carbon black (C), and combinations thereof.

Preferably, the support comprises at least one selected from zinc oxide (ZnO), zirconium dioxide ($ZrO_2$) and titanium dioxide ($TiO_2$) or a combination thereof; and more preferably the support is or comprises zirconium dioxide.

In an embodiment, the support comprises zirconium dioxide ($ZrO_2$) in an amount of at least 10 wt %, preferably at least 30 wt %, more preferably at least 50 wt %, even more preferably at least 80 wt %, and most preferably at least 90 wt % based on the total weight of the calcined supported catalyst.

In an embodiment, the support is zirconium dioxide or a combination of zirconium dioxide with another support in which zirconium dioxide is contained in an amount of at least 10 wt %, preferably at least 50 wt %, more preferably at least 80 wt %, and even more preferably at least 90 wt % based on the total weight of the support, the other support being selected from silica ($SiO_2$), alumina ($Al_2O_3$), gallium oxide ($Ga_2O_3$), cerium oxide ($CeO_2$), vanadium oxide ($V_2O_5$), chromium oxide ($Cr_2O_3$), titanium dioxide ($TiO_2$), magnesium oxide (MgO), zinc oxide (ZnO), tin oxide ($SnO_2$), carbon black (C), and combinations thereof; preferably the other support is selected from zinc oxide (ZnO), titanium dioxide ($TiO_2$), and combinations thereof.

A catalyst support can be porous or non-porous. In some embodiments a catalyst support can be provided in a particulate form of particles having a surface area (i.e BET surface area) as determined by $N_2$ sorption analysis according to ASTM D3663-03, in the range of about 20 m$^2$ g$^{-1}$ to about 400 m$^2$ g$^{-1}$, such as from 30 m$^2$ g$^{-1}$ to about 200 m$^2$ g$^{-1}$ as determined according to $N_2$ sorption analysis, a pore volume in the range of about 0.1 cm$^3$/g to about 10 cm$^3$/g, such as from about 0.2 cm$^3$ g$^{-1}$ to about 5 cm$^3$ g$^{-1}$.

The calcined supported catalyst has preferably a surface area (i.e BET surface area) as determined by $N_2$ sorption analysis according to ASTM D3663-03, in the range of about 20 m$^2$/g to about 400 m$^2$ g$^{-1}$, such as from 30 m$^2$ g$^{-1}$ to about 200 m$^2$ g$^{-1}$.

The catalyst can be combined with a catalyst support or other support medium through, for example impregnation, such that the catalyst can be coated on, deposited on, impregnated on or otherwise disposed adjacent to the catalyst support. For example, a supported catalyst can be synthesized by an impregnation step followed by a calcination step. The catalyst can be provided in technical shapes such as extrudates, granules, spheres, monoliths, or pellets and might contain additives such as lubricants, peptizers, plasticizers, porogens, binders, and/or fillers.

In a preferred embodiment the calcination step is performed at a temperature above 500 K (226.85° C.), preferably above 530 K (256.85° C.), more preferably above 550 K (276.85° C.), even more preferably above 570 K (296.85° C.).

The above catalyst is useful for the synthesis of methanol from hydrogen and carbon oxides or the reverse reaction thereof.

TEST METHODS AND DEFINITIONS

Activity for methanol synthesis reaction is determined using a home-made fixed-bed reactor set-up which has been described in detail previously (O. Martin and al., *ACS Catal.* 2015, 5, 5607-5616). Briefly, it comprises mass flow controllers to feed Ar, CO, $H_2$, and $CO_2$ (Messer, ≥99.997%), a stainless steel reactor (0.65 cm i.d.) equipped with a thermocouple placed in the reactor wall adjacent to the catalytic bed and heated by an oven, and an online gas chromatograph (Agilent 7890A) monitoring the outlet gas composition. For experiments in which the reaction conditions (i.e., temperature, pressure, R=CO/($CO_2$+CO), or molar feed $H_2$:$CO_2$) are varied, the individual conditions are maintained for 4 h. Prior to the reaction, $In_2O_3$ and ZnO catalysts are activated in Ar at 573 K and 0.5 MPa for 1 h. CuO—ZnO—$Al_2O_3$ is pretreated in 5 vol % $H_2$ in Ar at 503 K and 0.5 MPa for 1 h. Tests are conducted using a catalyst mass of 0.3 g (particle size: 0.050-0.075 mm), a temperature of 473-573 K, a pressure of 5.0 MPa, a total flow rate of 130 cm$^3$ STP min$^{-1}$.

If not stated differently, the syngas feed stream comprises 61.5 mol % $H_2$, 15.4 mol % $CO_2$, and 23.1 mol % Ar. In the case of CO co-feeding, the syngas feed stream contains 61.5 mol % $H_2$, 15.4 mol % CO+$CO_2$, and 23.1 mol % Ar. The CO fraction is expressed as R=CO/($CO_2$+CO) representing the mol % of CO based on the total molar content of the carbon oxides. R is varied is step-wise following the sequence: R=0, 20, 40, 60, 80, 100, and 0%.

In experiments, in which the molar feed $CO_2:H_2$ ratio is varied, a total flow rate of 146 cm$^3$ STP min$^{-1}$ is applied. The syngas feed stream composition is consecutively changed from 45.6 mol % $H_2$ and 22.8 mol % $CO_2$ (molar feed $H_2:CO_2=2$) to 54.7 mol % $H_2$ and 13.7 mol % $CO_2$ (molar feed $H_2:CO_2=4$), 60 8 mol % $H_2$ and 7.6 mol % $CO_2$ (molar feed $H_2:CO_2=8$), and 63 1 mol % $H_2$ and 5.3 mol % $CO_2$ (molar feed $H_2:CO_2=12$), and finally to 64.4 mol % $H_2$ and 4 mol % $CO_2$ (molar feed $H_2:CO_2=16$). The Ar content is kept constant at 31.6 mol %.

The mol % content of the reactants $H_2$, $CO_2$, and CO in the syngas feed stream and the mol % content of the reactants and the methanol product in the outlet are determined by an online gas chromatograph (Agilent 7890A) equipped with an flame ionization detector (FID) and a thermal conductivity detector (TCD).

Conversion of carbon dioxide in % is determined according to the following equation:

$$X_{CO_2} = \left(1 - \frac{A_{CO_2}}{A_{Ar} f_{c1,CO_2:Ar}}\right) \times 100$$

where $A_{CO_2}$ and $A_{Ar}$ are the integrated areas of the signals of $CO_2$ and Ar, respectively, in the gas chromatogram, and $f_{c1,CO_2:Ar}$ is the calibration factor determined for $CO_2$ taking the Ar signal at $X_{CO_2}=0\%$ as a reference.

Yield of methanol in % is calculated according to the following equation:

$$Y_{MeOH} = \frac{A_{MeOH}}{A_{Ar} f_{c2,MeOH:Ar}} \times 100\%$$

where $A_{MeOH}$ is the integrated area of the signal of methanol in the gas chromatogram, and $f_{c2,MeOH:Ar}$ is the calibration factor determined for methanol taking the Ar signal at $Y_{MeOH}=100\%$ conversion as a reference.

Selectivity to methanol in % is calculated according to the following equation:

$$S_{MeOH} = \frac{Y_{MeOH}}{X_{CO_2}} \times 100\%$$

Space-time yield refers to the grams of methanol produced per grams of catalyst and per hour and is calculated according to the following equation:

$$STY = \frac{F_{CO_2} M_{MeOH} Y_{MeOH}}{V_M W_{cat}}$$

where $F_{CO_2}$ is the volumetric flow of $CO_2$, $M_{MeOH}$ is the molecular mass of methanol, $V_m$ is the molar volume of an ideal gas at STP (=22.414 L mol$^{-1}$), $W_{cat}$ is the catalyst mass, The methanol formation rate per grams of $In_2O_3$ is determined through the following equation:

$$r = \frac{F_{CO_2} M_{MeOH} Y_{MeOH}}{V_M W_{cat} w_{In_2O_3}}$$

where $w_{In2O3}$ is the mass fraction of indium oxide in the catalyst determined by X-ray fluorescence spectroscopy.

Powder X-ray diffraction (XRD) analysis was performed using a PANalytical X'Pert Pro MPD instrument, utilizing Cu-K$\alpha$ radiation ($\lambda=0.1542$ nm), an angular step size of 0.033° 2θ, and a counting time of 8 s per step. The average particle size of $In_2O_3$ was estimated from the (222) reflection applying the Scherrer equation.

X-ray photoelectron spectroscopy (XPS) analysis was conducted using a Physical Electronics (PHI) Quantum 2000 X-ray photoelectron spectrometer featuring monochromatic Al-K$\alpha$ radiation, generated from an electron beam operated at 15 kV and 32.3 W, and a hemispherical capacitor electron-energy analyzer, equipped with a channel plate and a position-sensitive detector. The samples were firmly pressed onto indium foil patches, which were then mounted onto a sample platen and introduced into the spectrometer. The analysis was conducted at $2\times10^{-7}$ Pa, with an electron take-off angle of 45°, and operating the analyzer in the constant pass energy mode. Elemental concentrations were calculated from the photoelectron peak areas after Shirley background subtraction and applying the built-in PHI sensitivity factors.

The metal composition of the calcined samples was determined by X-ray fluorescence (XRF) spectroscopy using an Orbis Micro-EDXRF spectrometer equipped with a Rh source (15 kV, 500 μA) and a silicon drift detector.

Specific surface area and pore volume were determined from the sorption isotherm of $N_2$ at 77 K. The Brunauer-Emmett-Teller (BET) method was applied for calculating the specific surface area according to ASTM D3663-03 and the volume of gas adsorbed at saturation pressure was used to determine the pore volume.

EXAMPLES

The advantages of the present invention are illustrated by the following examples. However, it is understood that the invention is no means limited to the specific examples.

Example 1: Synthesis of a Catalyst Comprising $In_2O_3$ Impregnated on $ZrO_2$

The materials used were an indium salt, i.e., indium (III) nitrate hydrate ($In(NO_3)_3 \cdot xH_2O$, Alfa Aesar, 99.99%); a mainly monoclinic (NorPro, SZ 31164) or a purely cubic (synthesized according to the preparation procedure described below) $ZrO_2$ catalyst support, and deionized water.

The $ZrO_2$ catalyst support (Saint-Gobain NorPro, SZ 31164, extrudates having diameter 3-4 mm and length 4-6 mm) in monoclinic structure (with ~5 wt % cubic phase) was used, having the following specifications (prior to mortar crushing):
specific surface area of 85 m$^2$ g$^{-1}$ ($N_2$ sorption analysis)
pore volume of 0.29 cm$^3$ g$^{-1}$ ($N_2$ sorption analysis)
Synthesis of the cubic $ZrO_2$ catalyst support: 5.21 g of zirconyl nitrate hydrate ($ZrO(NO_3)_2 \cdot xH_2O$, Acros Organics, 99.5%) was dissolved in 500 ml of deionized water under stirring. 31 ml of ethylene diamine (Fluka, 99.5%) was added dropwise. The slurry was stirred for further 30 min and then it was refluxed for 6 h. The obtained solution was filtered and the precipitate was washed with 2 l of deionized water. After drying at 338 K in static air, the resulting the material was calcined in static air at 873 K (599.85° C.) for 2 h with a heating rate of 2 K min$^{-1}$.

Preparation of the supported catalysts (11 wt % $In_2O_3$ loading): 0.76 g of indium salt was dissolved in a mixture of 70 ml of ethanol absolute (Sigma-Aldrich, 99.8%) and 24 ml of ethanol water under stirring. 2 g of either crushed as-received monoclinic or as-prepared cubic zirconium dioxide (both sieve fraction <0.075 mm) were added to the solution, which was mixed by a magnetic stirrer for 5 h. The solvent was removed in a rotary evaporator at 333 K (59.85° C.). The resulting material was dried at 338 K (64.85° C.) in static air overnight and finally calcined in static air at 573 K (299.85° C.) for 3 h applying a heating rate of 5 K min$^{-1}$.

The produced catalyst was used in a methanol synthesis reaction.

The below Table 1 compares the results for STY, selectivity, and $CO_2$ conversion obtained for the catalyst of the invention compared to other catalysts in prior art studies. Reaction conditions: T=573 K, P=5 MPa, GHSV=21,000 h$^{-1}$, molar $H_2$:$CO_2$=4:1.

TABLE 1

| Catalyst | T[K] | P[MPa] | STY(*) | $S_{MeOH}$[%] | $X_{CO_2}$[%] | Ref |
|---|---|---|---|---|---|---|
| $In_2O_3$/$ZrO_2$ (monoclinic) | 573 (299.85° C.) | 5.0 | 0.321 | 99.9 | 5.6 | This work |
| $In_2O_3$/$ZrO_2$ (cubic) | 573 (299.85° C.) | 5.0 | 0.330 | 99.9 | 5.8 | This work |
| Cu—ZnO—$Ga_2O_3$/$SiO_2$ | 543 (269.85° C.) | 2.0 | 0.349 | 99.5 | 5.6 | [1] |
| Au—ZnO—$ZrO_2$ | 493 (219.85° C.) | 8.0 | 0.019 | 99.9 | 2.0 | [2] |
| Ag—ZnO—$ZrO_2$ | 493 (219.85° C.) | 8.0 | 0.015 | 97.0 | 2.0 | [2] |
| Pd—ZnO/CNT | 523 (249.85° C.) | 3.0 | 0.037 | 99.6 | 6.3 | [3] |
| Cu/TaC | 553 (279.85° C.) | 6.0 | 0.042 | 18.2 | 1.4 | [4] |
| $LaCr_{0.5}Cu_{0.5}O_3$ | 523 (249.85° C.) | 2.0 | 0.314 | 90.8 | 10.4 | [5] |

(*)STY given in $g_{MeOH}$ h$^{-1}$ $g_{cat}^{-1}$

[1] Toyir, J.; Ramírez de la Piscina, P.; Fierro, J. L. G.; Homs, N.; Appl. Catal, B 2001, 29, 207-215.
[2] Słoczyński, J.; Grabowski, R.; Kozlowska, A.; Olszewski, P.; Stoch, J.; Skrzypek, J.; Lachowska, M.; Appl. Catal, A 2004, 278, 11.
[3] Liang, X.-L.; Dong, X.; Lin, G.-D.; Zhang, H.-B.; Appl. Catal, B 2009, 88, 315-322.
[4] Dubois, J.-L.; Sayama, K.; Arakawa, H.; Chem. Lett. 1992, 21, 5-8.
[5] Jia, L.; Gao, J.; Fang, W.; Li, Q.; Catal Commun. 2009, 10, 2000-2003.

Figure 2:
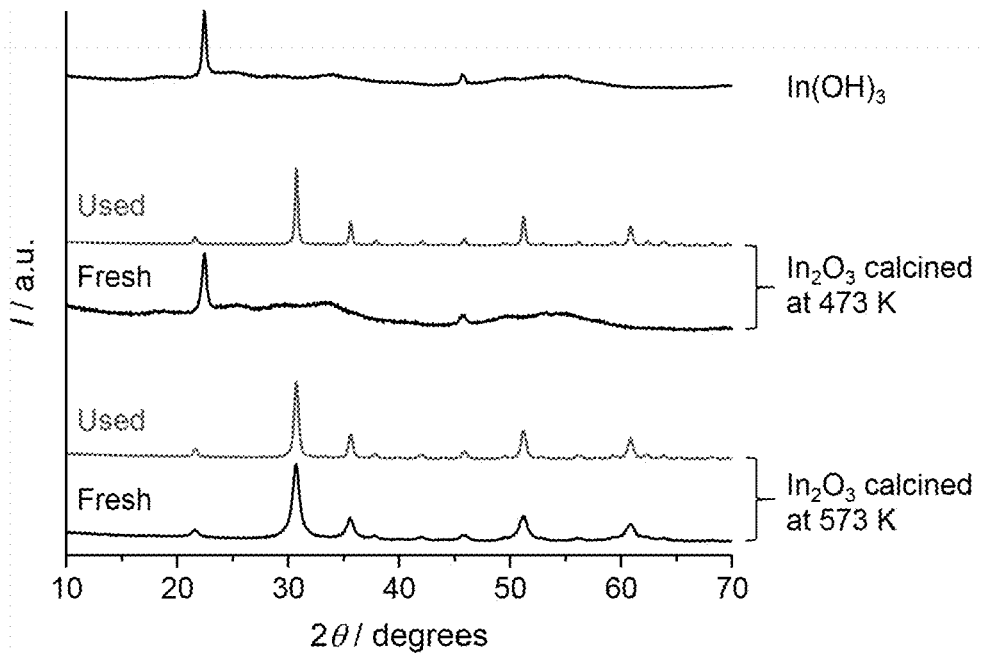
FIG. 2 displays the X-ray powder diffraction (XRD) analysis of uncalcined $In(OH)_3$ retrieved according to the invention by co-precipitation and of the bulk catalysts $In_2O_3$ according to the invention calcined at different temperatures before and after methanol synthesis reaction under standard reaction conditions.
Figure 3:
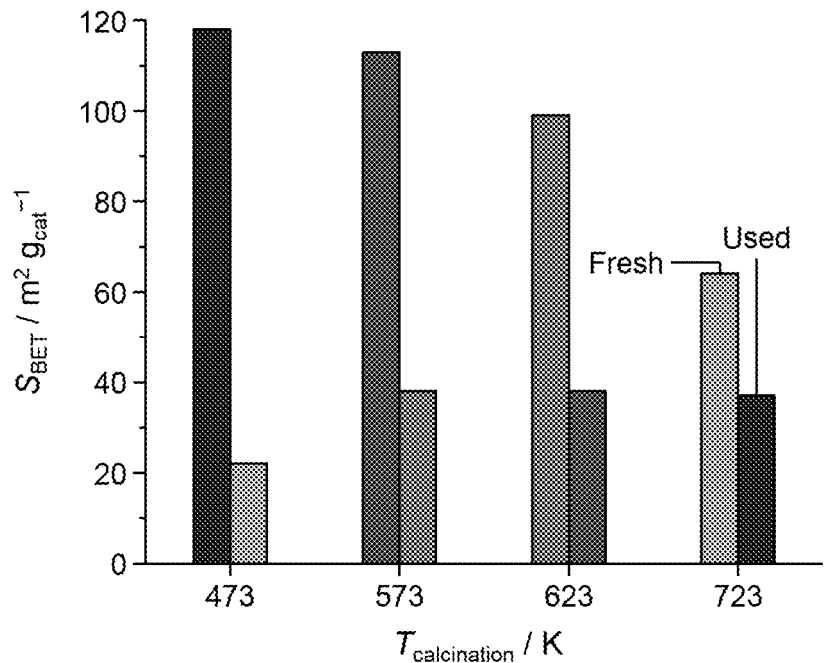
FIG. 3 shows the BET surface area analysis of the bulk catalysts $In_2O_3$ according to the invention calcined at different temperatures before and after methanol synthesis reaction under standard reaction conditions.

Example 2: Effect of the Calcination Temperature on the $In_2O_3$ Catalyst Activity The impact of the calcination temperature on the catalyst activity has been evaluated using samples of $In_2O_3$ calcined at different temperature. The samples were calcined at 473 K (199.85° C.), 573 K (299.85° C.), 623 K (349.85° C.) and 723 K (449.85° C.) for 3 h using a heating rate of 5 K min$^{-1}$. Results are shown in FIGS. 1 to 3. Reaction conditions: T=573 K, P=5 MPa, GHSV=21,000 h$^{-1}$, molar $H_2$:$CO_2$=4:1.

In FIG. 1, it can be seen that the sample calcined at 473 K (199.85° C.) showed a lower activity than the other ones. The XRD analysis given in FIG. 2 showed that the sample calcined at 473 K (199.85° C.) retains the initial $In(OH)_3$ phase which is converted into $In_2O_3$ upon reaction. The BET surface area analysis given in FIG. 3 demonstrates that, except for the sample calcined at 473 K (199.85° C.), different calcination temperatures generate materials with distinct initial surface area, which decreases to the same value after reaction. Considering the increasing activity with ascending calcination temperature (FIG. 1), it can be concluded that the concentration of active sites is enhanced with increasing temperature of calcination.

Example 3: Effect of the Reaction Temperature in Methanol Synthesis on the Catalyst Activity The activity of the following catalysts in methanol synthesis at different temperatures was tested:

a—Cu—ZnO-$Al_2O_3$
b—$In_2O_3$
c—ZnO $In_2O_3$ and ZnO were prepared through calcination of $In(OH)_3$ and $Zn(OH)_2$ obtained by precipitation. The latter comprised the dissolution of 6.1 g of $In(NO_3)_3$.x$H_2O$ (Alfa Aesar, 99.99%) or 4.7 g of $Zn(NO_3)_2$.$6H_2O$ (Acros Organics, 98%) in a mixture of deionized water (24 cm$^3$) and ethanol (Sigma-Aldrich, 99.8%, 70 cm$^3$), followed by the addition of a solution containing the precipitating agent, i.e., 18 cm$^3$ of 25 wt. % $NH_4OH$ (aq, Sigma-Aldrich) in 54 cm$^3$ of ethanol. The obtained slurry was aged for 10 min at 353 K, filtered, and washed with 2 L of deionized water. The precipitate was dried at 338 K for 12 h prior to calcination in static air at 573 (heating rate: 5 K min$^{-1}$) for 3 h.

The Cu—ZnO—$Al_2O_3$ catalyst was synthesized via coprecipitation mixing under vigorous stirring 100 cm$^3$ of a 1 M aqueous metal salt solution, containing $Cu(NO_3)_2$.$3H_2O$ (Sigma-Aldrich, 98%), $Zn(NO_3)_2$.$6H_2O$, and $Al(NO_3)_3$.$9H_2O$ (Alfa Aesar, 98%) in a molar Cu:Zn:Al ratio of 6:3:1, and 200 cm$^3$ of a 1 M aqueous solution of $Na_2CO_3$ (Acros Organics, 99.8%), reaching a final pH of 8. The slurry was aged at 338 K for 2 h. The slurry was filtered, washed 2 L of deionized water. The precipitate was dried at 338 K for 12 h prior to calcination in static air at 573 (heating rate: 5 K min$^{-1}$) for 3 h.

Figure 4:
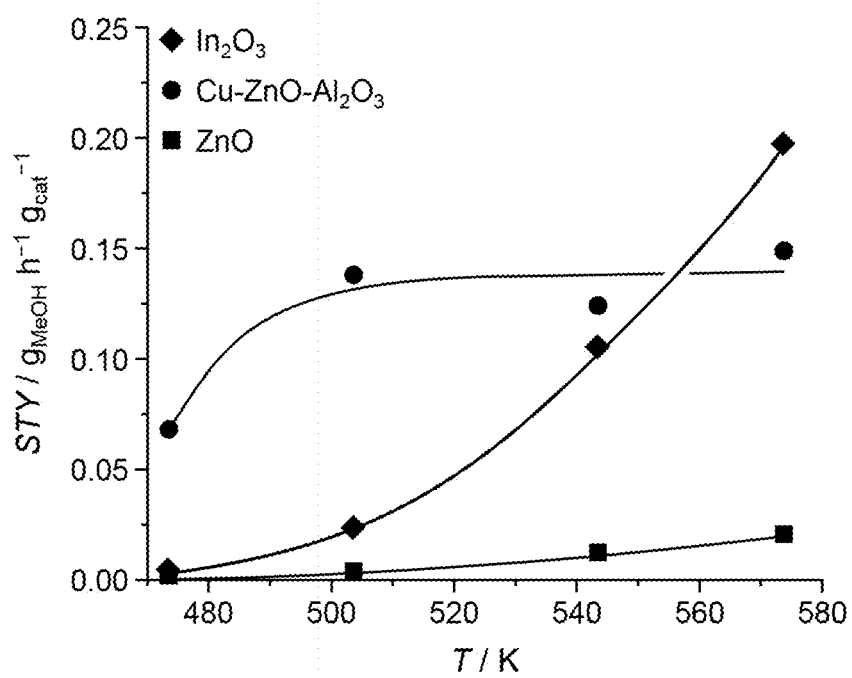
FIG. 4 is a graph plotting the space-time yield of different catalysts (including the bulk catalyst $In_2O_3$ according to the invention) as a function of the reaction temperature in methanol synthesis reaction under standard reaction conditions.

The results given in FIG. 4 have been obtained at a pressure of 5 MPa with a GHSV of 21,000 h$^{-1}$ and with a molar $CO_2$:$H_2$ ratio of 1:4. They show the activity of the Cu—ZnO—$Al_2O_3$, ZnO, and $In_2O_3$ catalysts at different reaction temperatures.

From these results, it can be seen that at 573 K (299.85° C.) $In_2O_3$ displays outstanding activity with respect to the other benchmark catalysts in methanol synthesis. It can be seen that Cu—ZnO-$A_2O_3$ suffers from $H_2O$ inhibition above 503 K (229.85° C.). Without being bound by a theory, it is believed that the higher activity of $In_2O_3$ at 573 K (299.85° C.) is due to the absence of this phenomenon.

Figure 5:
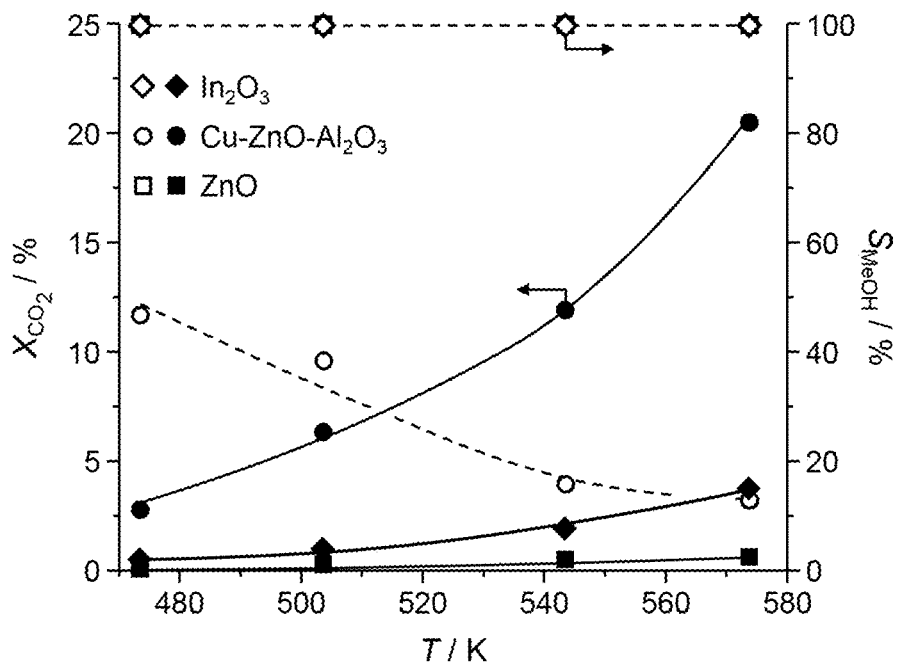
FIG. 5 is a graph plotting the $CO_2$ conversion and methanol selectivity of different catalysts (including the bulk catalyst $In_2O_3$) as a function of the reaction temperature in a methanol synthesis reaction under standard reaction conditions.

$CO_2$ conversion and selectivity to methanol are given in FIG. 5. The selectivity to methanol of 100% for $In_2O_3$ indicates that $In_2O_3$ is not active for the RWGS under the tested conditions. The same selectivity was found for ZnO.

For Cu—ZnO—Al$_2$O$_3$, the CO$_2$ conversion increases while the selectivity to methanol decreases with ascending temperature because this catalyst is mainly active for the RWGS under the operation conditions applied in this study.

Example 5: Influence of the Interaction with the Support

Figure 6:
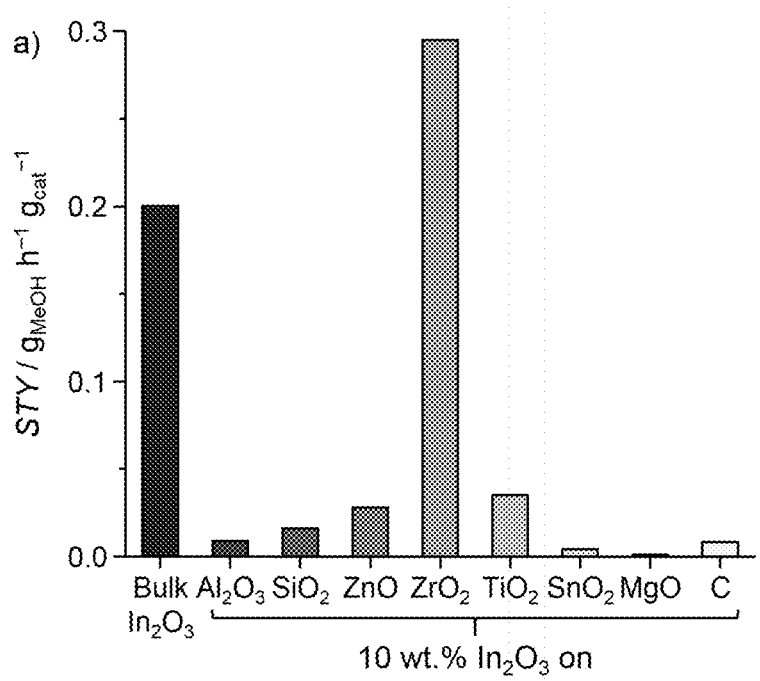
FIG. 6 is a graph plotting the space-time yield for the bulk catalyst $In_2O_3$ and for $In_2O_3$ supported on different catalyst supports according to this invention evaluated under standard reaction conditions.

The effect of several materials (silica (SiO2), gamma alumina (Al2O3), zirconium dioxide (ZrO2), titanium dioxide (TiO2), magnesium oxide (MgO), zinc oxide (ZnO), tin oxide (SnO2), carbon black (C)) as support for the indium oxide catalyst have been tested. Results are given in FIG. 6. Reaction conditions: T=573 K, P=5 MPa, GHSV=21,000 h$^{-1}$, molar H$_2$:CO$_2$=4:1. Although the reaction rates per grams of In$_2$O$_3$ contained in the supported catalysts are improved in case of using ZnO, TiO$_2$ (25 wt % rutile-75 wt % anatase), or ZrO$_2$ as catalyst support with respect to the bulk catalyst In$_2$O$_3$, only the ZrO$_2$-supported In$_2$O$_3$ catalyst also provides a sufficient space-time yield which even exceeds the one of the bulk In$_2$O$_3$ catalyst by 50% (FIG. 6). In view of the low or complete inactivity of all other supports for methanol synthesis, this result demonstrates a strong synergistic effect of the In$_2$O$_3$ catalyst and the ZrO$_2$ catalyst support. All supports were also tested without containing In$_2$O$_3$ and none of them did show any activity for CO$_2$ hydrogenation to methanol under the used reaction conditions.

Figure 7:
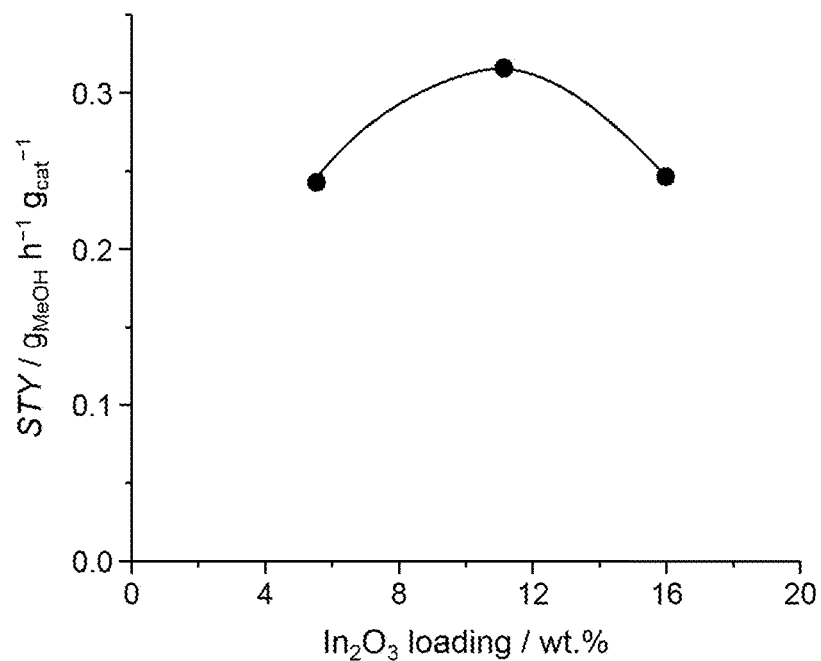
FIG. 7 is a graph plotting the space-time yield of the bulk catalyst $In_2O_3$ and of the supported catalyst $In_2O_3$ on $ZrO_2$ carrier according to this invention as a function of the $In_2O_3$ loading.

The optimal loading of In$_2$O$_3$ on the ZrO$_2$-supported catalysts of the examples is shown in FIG. 7 and was found to be 11 wt % based on the calcined supported catalyst.

Example 6: Effect of Total Pressure

Figure 8:
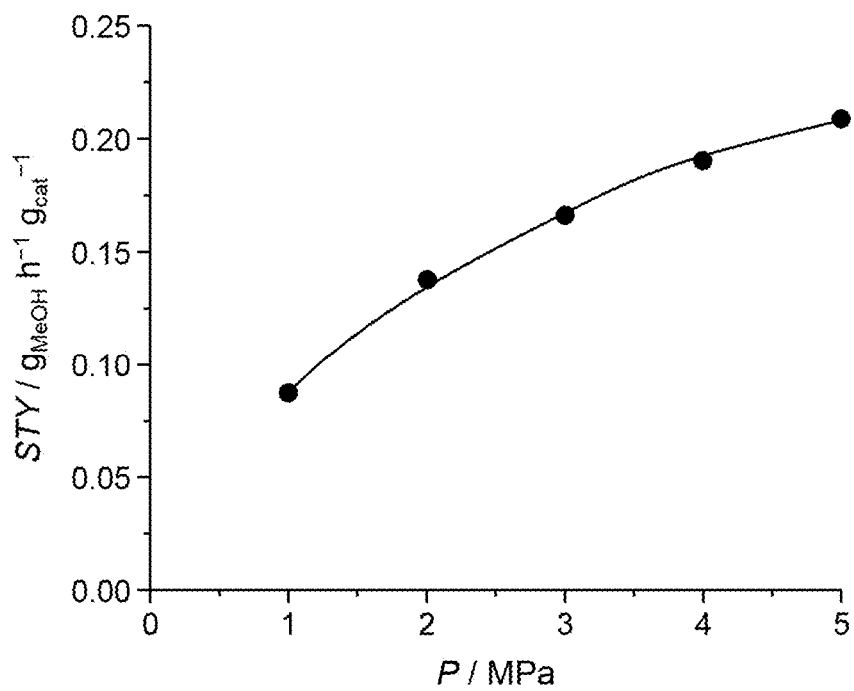
FIG. 8 depicts the space-time yield of methanol over the bulk catalyst $In_2O_3$ according to the invention as a function of the total pressure under standard reaction conditions.

FIG. 8 displays the behavior of the bulk In$_2$O$_3$ catalyst in CO$_2$ hydrogenation under different total pressures. Reaction conditions: T=573 K, GHSV=21,000 h$^{-1}$, molar H$_2$:CO$_2$=4:1. The reaction rate increases by a factor of approximately 3 when the pressure is elevated from 1 to 5 MPa.

Example 7: Effect of Molar Feed H$_2$:CO$_2$ Ratio

Figure 9:
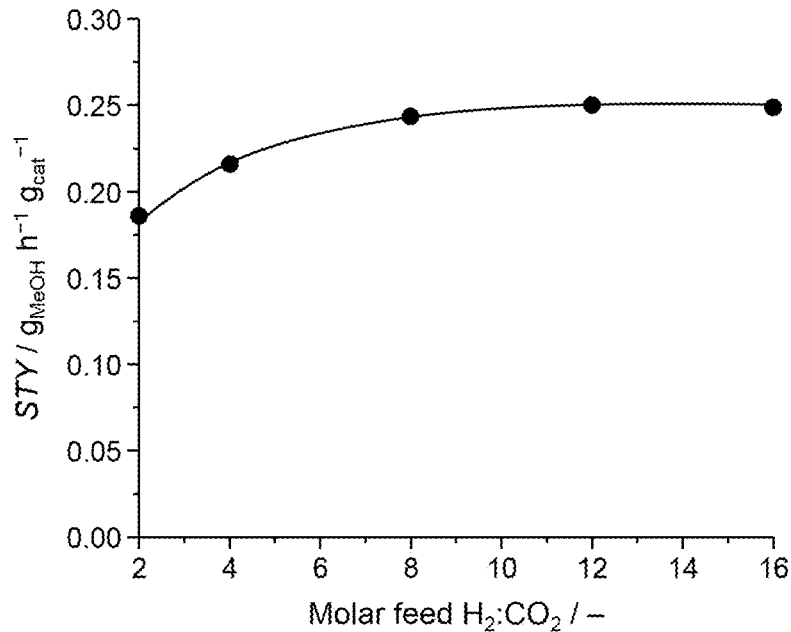
FIG. 9 shows the space-time yield of methanol over the bulk catalyst $In_2O_3$ according to the invention as a function of the molar hydrogen to carbon dioxide ratio in the feed stream under standard reaction conditions.

The CO$_2$ hydrogenation activity of the bulk In$_2$O$_3$ catalyst was tested under different molar H$_2$:CO$_2$ ratios in the syngas feed stream (FIG. 9). Reaction conditions: T=573 K, P=5 MPa, GHSV=21,000 h$^{-1}$. The results reveal a beneficial effect when the molar H$_2$:CO$_2$ ratio in the feed stream is increased from 2 to 8. Further increase of this ratio does not elevate the space-time yield.

Example 8: Effect of the Syngas Composition

Figure 10:
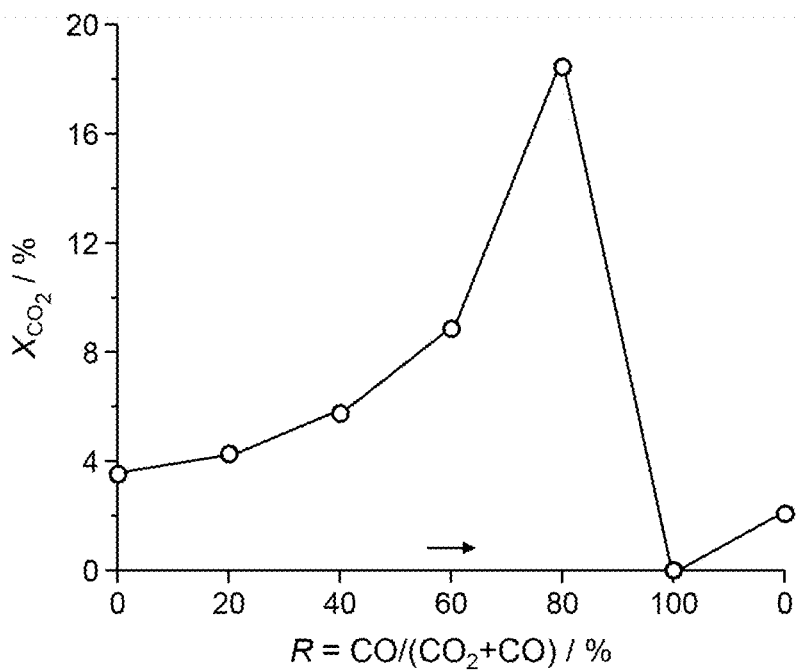
FIG. 10 is a graph plotting the conversion of $CO_2$ over the bulk catalyst $In_2O_3$ according to this invention as a function of the syngas composition in which the CO and $CO_2$ concentrations were varied.

The effect of the syngas composition was studied at the reaction temperature of 573 K (299.85° C.). The results are given in FIG. 10. The CO/CO$_2$ composition in the syngas feed stream was step-wise changed from R=CO/(CO$_2$+CO)=0 to 100% and back to 0% (based on the molar ratio). Reaction conditions: T=573 K, P=5 MPa, GHSV=21,000 h$^{-1}$, molar H$_2$:(CO+CO$_2$)=4:1.

It can be seen that the In$_2$O$_3$ catalyst performs optimally when using a syngas feed stream containing 20 mol % of CO$_2$ and 80 mol % of CO based on the total molar content of carbon oxide of the syngas feed stream. The optimization of the feed stream allows a CO$_2$ conversion from 3.5% to 18.0%.

The catalyst is inactive in a pure CO syngas stream.

Example 9: Vacancy Formation and CO$_2$ Adsorption

Figure 11:
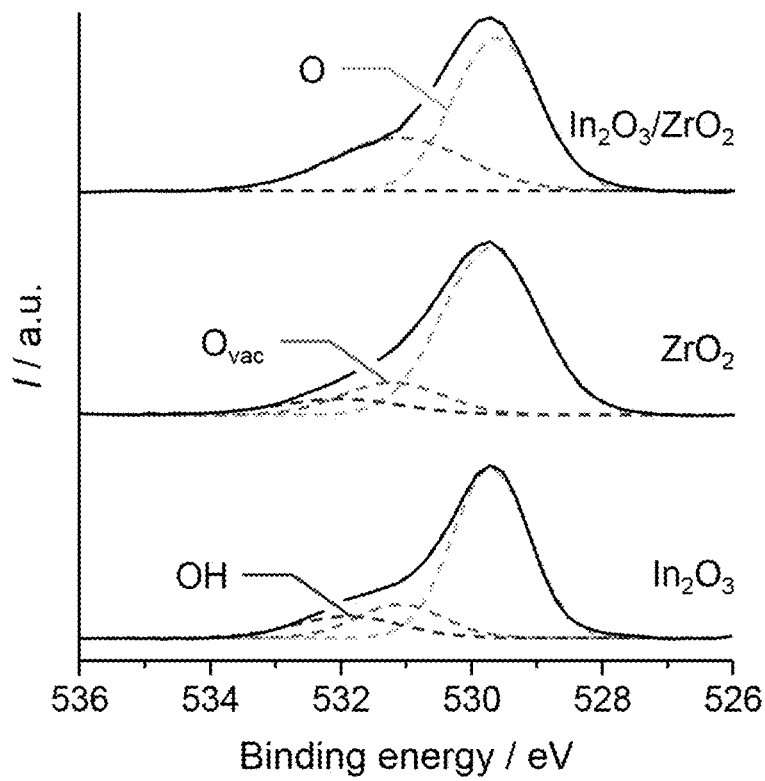
FIG. 11 displays the core-level O1s signals from XPS analysis of the bulk catalyst $In_2O_3$, the catalyst support $ZrO_2$, and the supported catalyst $In_2O_3$ on $ZrO_2$ according to this invention. Deconvolution of the spectral features reveals the presence of oxygen atoms next to an oxygen vacancy at the catalyst surface in all materials which is largely amplified in the supported $In_2O_3$/$ZrO_2$ catalyst with respect to the bulk $In_2O_3$ catalyst or the pure $ZrO_2$ carrier.

XPS can be used to determine the amount of oxygen surface defects, which are thought to be essential for the activity of In$_2$O$_3$-based catalysts, by calculating the atomic ratio of oxygen and indium. In a stoichiometric oxide, the oxygen-to-indium ratio is 1.5. In the case of the used bulk In$_2$O$_3$ catalyst this ratio is 0.78. This substoichiometric ratio points to an oxygen-defective surface. Semi-quantitative information of the oxygen defects is further gained from the core-level O1s signals as depicted in FIG. 11. After deconvolution, the peak at ~530.9 eV (O$_{vac}$) is assigned to oxygen atoms adjacent to oxygen vacancies. This signal is found in both the bulk In$_2$O$_3$ catalyst and the pure monoclinic ZrO$_2$ catalyst support evidencing the presence of oxygen vacancies. The supported In$_2$O$_3$/ZrO$_2$ (monoclinic) catalyst provides a signal at this binding energy which is much larger compared to the sum of the individual components. It is concluded that this is related to the synergistic effect observed for the activity (FIG. 6).

Example 10: Stability of In$_2$O$_3$

Figure 12:
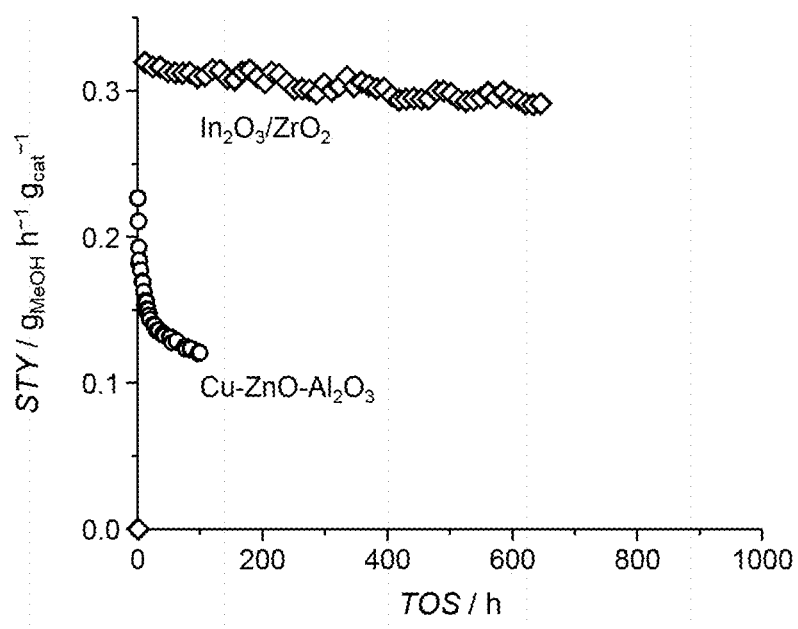
FIG. 12 demonstrates the highly stable performance of the supported catalyst $In_2O_3$ on $ZrO_2$ according to this invention for 1,000 h with respect to the state-of-the-art Cu—ZnO—$Al_2O_3$ catalyst under standard reaction conditions.

FIG. 12 reports the catalytic data collected during a 1000-h test to evaluate the stability of the indium oxide supported on monoclinic zirconium oxide (in which inidium oxide is comprised to 11 wt % based on the total weight of the calcined supported catalyst) catalyst according to the invention. The loss in STY was of 8% only within the first 400 h on stream and the activity remained stable thereafter, while the selectivity remained at 100% throughout the experiment which demonstrates a high stability of this catalyst. In contrast, the Cu—ZnO—Al$_2$O$_3$ benchmark catalyst loses 44% of its initial activity within the first 100 h on stream. Reaction conditions: T=573 K, P=5 MPa, GHSV=21,000 h$^{-1}$, molar H$_2$:CO$_2$=4:1.

Example 11: Effect of Activation Procedure

A bulk catalyst In$_2$O$_3$ was activated through different methods prior to testing the catalytic activity at T=573 K, P=5 MPa, GHSV=21,000 h$^{-1}$, molar H$_2$:CO$_2$=4:1. Upon the first method, the catalyst was activated in a flow (100 cm$^3$ STP min$^{-1}$) of a mixture containing 5 mol % H$_2$ and 95 mol % Ar based on the total molar content of the feed stream. The obtained space-time yield was 0.169 g$_{MeOH}$ h$^{-1}$ g$_{cat}^{-1}$. Upon a second method, the catalyst was activated in a flow (100 cm$^3$ STP min$^{-1}$) of only Ar. The resulting space-time yield according to this procedure was 0.195 g$_{MeOH}$ h$^{-1}$ g$_{cat}^{-1}$. In both cases, the temperature was raised from 303 to 573 K by 5 K min$^{-1}$. This result demonstrates that a thermal activation in inert gas atmosphere is preferred over an activation in reducing gas (such as H$_2$).

The invention claimed is:
1. A process for methanol synthesis comprising:
providing a syngas feed stream comprising hydrogen and carbon oxides selected from the group consisting of carbon dioxide and a mixture of carbon dioxide and carbon monoxide, wherein carbon dioxide represents from 1 to 50 mol % of the total molar content of the feed stream, carbon monoxide is contained from 0 to 85 mol % of the total molar content, and H$_2$ is comprised from 5 to 95 mol % of the total molar content of the feed stream;
providing a supported catalyst comprising indium oxide (In$_2$O$_3$) deposited on a support wherein the support comprises zirconium dioxide or is zirconium dioxide;
contacting said syngas feed stream with said supported catalyst at a reaction temperature of at least 373 K (99.85° C.) and under a pressure of at least 1 MPa; and
recovering the methanol effluents.

2. The process according to claim 1, wherein the supported catalyst is a calcined supported catalyst and the support comprises zirconium dioxide ($ZrO_2$) in an amount of at least 30 wt %, based on the total weight of the calcined supported catalyst.

3. The process according to claim 1 wherein the reaction temperature is at least 463 K (189.85° C.).

4. The process according to claim 1 wherein the pressure is at least 2 MPa.

5. The process according to claim 1, wherein the syngas feed stream comprises hydrogen and a mixture of carbon dioxide and carbon monoxide and the molar ratio of carbon monoxide to carbon dioxide in the syngas feed stream is at least 1:10.

6. The process according to claim 1, wherein the syngas feed stream comprises hydrogen and carbon oxides that are selected from the group consisting of carbon dioxide and a mixture of carbon dioxide and carbon monoxide and the molar ratio of hydrogen to carbon dioxide in the syngas feed stream is at least 1:1.

7. The process according to claim 1, wherein the supported catalyst exhibits a molar surface oxygen-to-indium ratio below 1.5 as determined from the atomic concentrations by X-ray photoelectron spectroscopy.

8. The process according to claim 1, wherein the supported catalyst is prepared by a process involving a calcination step at a temperature above 500 K (226.85° C.).

9. The process according to claim 1, wherein the supported catalyst is a calcined supported catalyst and the indium oxide content in the form of $In_2O_3$ ranges from 5 to 20% by weight, based on the total weight of the calcined supported catalyst.

10. The process according to claim 1, wherein the process is carried out for more than 100 hours without replacement or reactivation of the supported catalyst.

11. The process according to claim 1, wherein prior to the reaction the supported catalyst is activated in situ by raising the temperature to the reaction temperature in a flow of a gas feed stream for activation selected from the group consisting of inert gases, hydrogen, carbon monoxide, carbon dioxide and mixture thereof.

* * * * *